(12) United States Patent
Hsieh et al.

(10) Patent No.: US 10,172,919 B2
(45) Date of Patent: Jan. 8, 2019

(54) METHOD FOR TREATING INFLUENZA A VIRUS INFECTION

(71) Applicant: ACADEMIA SINICA, Taipei (TW)

(72) Inventors: Shie-Liang Hsieh, Taipei (TW); Yung-Chi Chang, Taipei (TW); Ming-Ting Huang, New Taipei (TW)

(73) Assignee: ACADEMIA SINICA, Nankang Taipei (TW)

( * ) Notice: Subject to any disclaimer, the term of this patent is extended or adjusted under 35 U.S.C. 154(b) by 46 days.

(21) Appl. No.: 15/537,051

(22) PCT Filed: Dec. 29, 2015

(86) PCT No.: PCT/US2015/067870
§ 371 (c)(1),
(2) Date: Jun. 16, 2017

(87) PCT Pub. No.: WO2016/109541
PCT Pub. Date: Jul. 7, 2016

(65) Prior Publication Data
US 2017/0360884 A1      Dec. 21, 2017

Related U.S. Application Data

(60) Provisional application No. 62/097,581, filed on Dec. 29, 2014.

(51) Int. Cl.
*A61K 39/00* (2006.01)
*A61K 38/17* (2006.01)
*C07K 14/705* (2006.01)

(52) U.S. Cl.
CPC ...... *A61K 38/177* (2013.01); *C07K 14/70578* (2013.01); *C07K 2319/30* (2013.01)

(58) Field of Classification Search
None
See application file for complete search history.

(56) References Cited

U.S. PATENT DOCUMENTS

| | | |
|---|---|---|
| 2005/0124045 A1 | 6/2005 | Sun et al. |
| 2009/0181912 A1 | 7/2009 | Wang et al. |
| 2012/0189627 A1 | 7/2012 | Heavner |
| 2014/0275489 A1 | 9/2014 | Stevis et al. |
| 2014/0308296 A1 | 10/2014 | Riteau et al. |

*Primary Examiner* — Michelle S Horning
(74) *Attorney, Agent, or Firm* — Muncy, Geissler, Olds & Lowe, P.C.

(57) ABSTRACT

Disclosed herein is a method of treating influenza A virus (IAV) infection by a fusion protein. According to some embodiments of the present disclosure, the fusion protein comprises a HBD peptide and a IgG1 Fc region. According to other embodiments of the present disclosure, the fusion protein comprises a DcR3 protein and a IgG1 Fc region. The present fusion protein is found to possess inhibitory effects on IAV-induced secretion of the inflammatory cytokine, and IAV-induced infiltration of inflammatory cell into the lung tissue. Accordingly, the fusion protein is useful for developing a medicament for the treatment or prophylaxis of IAV infection and/or ameliorating pulmonary injury caused by excessive inflammation associated with IAV infection in a subject.

16 Claims, 11 Drawing Sheets

Specification includes a Sequence Listing.

US 10,172,919 B2

METHOD FOR TREATING INFLUENZA A VIRUS INFECTION

BACKGROUND OF THE INVENTION

1. Field of the Invention

The present disclosure in general relates to the field of treating infection. More particularly, the present disclosure relates to a method for the treatment or prophylaxis of influenza A virus infection.

2. Description of Related Art

Influenza A virus (IAV) is a negative-sense, single-stranded, segmented RNA virus. Seasonal IAV infections cause significant morbidity and mortality that leads to estimated 250,000-500,000 deaths worldwide, and over 35,000 deaths in the United States annually. For healthy children and adults, IAV infection is typically a moderately severe illness. However, it would cause very serious illness for those immunocompromised people, such as unhealthy or elderly people. One of the IAV-associated symptoms that place people at high risk is chronic lung diseases (e.g., asthma, emphysema, chronic bronchitis, bronchiectasis, or cystic fibrosis), which are mostly caused by excessive inflammation. It is known that aside from the bronchial and alveolar epithelial cells, the primary target cells for IAV infection and replication, macrophages also play a critical role in the IAV-induced pulmonary inflammation. Once infected by IAV, macrophages rapidly produce type I interferon (e.g., interferon-α, and interferon-β), pro-inflammatory cytokines (e.g., TNF-α, IL-6, and IL-1β), and chemokines (e.g., MCP-1, MIP-1α, RANTES and IP-10), all of which are responsible for the recruitments of leukocytes into pulmonary tissues and accordingly, resulting in tissue injury, edema, and pulmonary dysfunctions. Thus, macrophages are generally regarded as one of the key players in IAV-induced pulmonary injury and mortality in victims.

Decoy receptor 3 (DcR3), also known as tumor necrosis factor receptor superfamily member 6B (TNFRSF6B), TR6 and M68, is a member of the TNF receptor superfamily. For the lack of transmembrane domain, DcR3 is expressed as a soluble protein. As of today, the protein is known to play a regulatory role in various signaling pathways and is involved in different cellular events: (1) suppressing Fas-induced cell death; (2) suppressing LIGHT-mediated T cell activation; (3) inducing angiogenesis; and (4) modulating the activation and differentiation of monocytes to dendritic cell, macrophage, and osteoclast. Further, DcR3 is found to be overexpressed in various tumors and inflammatory tissues.

Given the fact that IAV infection continues to pose a major threat to the human population and less is known in how to prevent or modulate tissue injury caused by the disease, there exists in the related art a need for an improved method that provides treatment or prophylaxis to IAV infection and thereby prevents the infected subject from developing any subsequent tissue injury.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method for the treatment or prophylaxis of IAV infection in a subject. The method comprises administering to the subject a therapeutically effective amount of a fusion protein, which comprises a first peptide consisting of SEQ ID NO: 4, and a human IgG1 Fc region coupling to the first peptide.

Another aspect of the present disclosure pertains to a method of ameliorating the pulmonary injury in a subject in need thereof; specifically, the subject is infected by IAV infection and suffers from the excessive inflammation induced by IAV. The method comprises administering to the subject a therapeutically effective amount of a fusion protein, which comprises a first peptide consisting of SEQ ID NO: 4, and a human IgG1 Fc region coupling to the first peptide.

According to some embodiments of the present disclosure, the fusion protein further comprises a second peptide consisting of SEQ ID NO: 5 and a third peptide consisting of SEQ ID NO: 6, in which the second and third peptides are respectively disposed at and connected to the upstream and downstream of the first peptide consisting of SEQ ID NO: 4.

According to some embodiments of the present disclosure, the fusion protein is administered in an amount of about 0.5 to 5 mg/Kg body weight per dose. In one preferred example, the amount is about 0.8 to 1 mg/Kg body weight per dose. According to other embodiments of the present disclosure, the total dosage for a full course of treatment of the fusion protein is about 1 to 10 mg/Kg; preferable, the total dosage is about 1.6 to 2 mg/Kg body weight.

Accordingly to one embodiment of the present disclosure, the fusion protein is administrated by a route selected from the group consisting of oral, enteral, nasal, topical, transmucosal, and parenteral administration. In general, the parental administration is any of intramuscular, intravenous, or intraperitoneal injection.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1A:
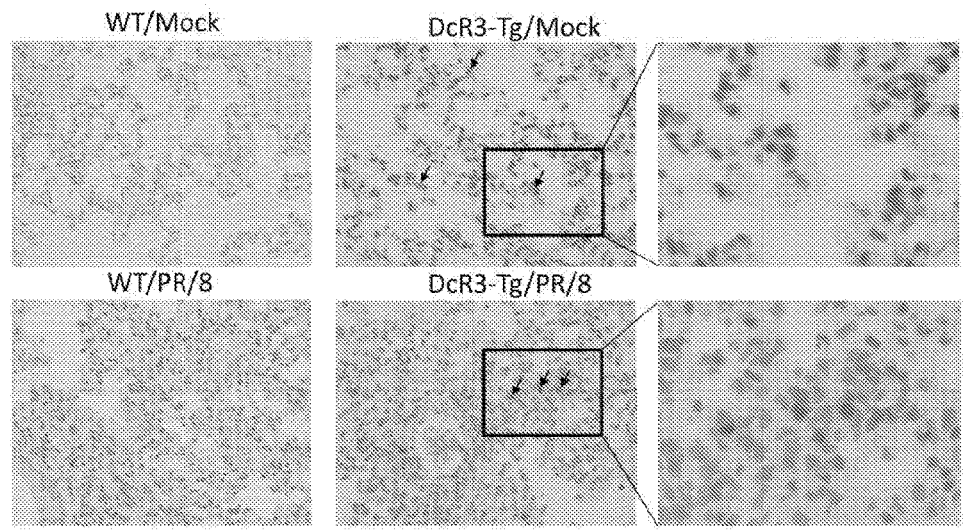
FIGS. 1A-1C are data of histochemiscal staining and enzyme-linked immunosorbent assay (ELISA) respectively depicting the expression of DcR3 in lung tissue (FIG. 1A), serum (FIG. 1B), and bronchoalveolar lavage fluid (BALF, FIG. 1C) of wild-type (WT) or DcR3-trangenic (DcR3-Tg) mice according to Example 1 of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "peptide" herein refers to a linear chain having at least two amino acid residues linked by peptide bonds. The amino acids making up a peptide may be any of the 20 standard genetically-encoded amino acids, other naturally occurring amino acids, unnatural amino acids, or chemically derivatized amino acids, and may exist as L form isomers or D form isomers. In the present disclosure, the peptide comprises amino acid residues raging in length from 2 to about 300 residues; preferably, 2 to 260 residues. A peptide may be obtained using conventional techniques known in the art. For example, a peptide may be synthesized or obtained from a native or recombinant protein by enzymatic digestion.

The terms "protein" and "polypeptide" are used interchangeably herein that refers to a biological molecule consisting of one or more peptides, regardless of post-translational modification. Each peptide in a protein may be a subunit. The protein or polypeptide may be in a native or modified form, and may exhibit a biological function or characteristics.

The term "fusion protein" herein refers to a combination of two proteins or peptides joined in any manner or by any type of linkage, covalent, electrostatic, hydrophobic-interaction, affinity-type, or otherwise, that maintains the linkage between the partners, prevents cleavage of the linkage during the procedural steps that are followed in the practice of this invention, and leaves the binding characteristics of the protein substantially unchanged. A preferred kind of fusion protein for the purpose of this invention is a peptide made from a recombinant gene that contains portions of two or more different genes, the genes being joined so that their coding sequences are in the same reading frame, i.e., so that the genetic apparatus reads the gene fusion as a single gene. This type of fusion protein is also known as a hybrid protein or a chimeric protein.

The terms "Fc region" and "fragment crystallizable region" are used interchangeably herein and refer to a C-terminal region of an immunoglobulin (e.g., IgG1, IgG2, IgG3, or IgG4) heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region may also include any portion of a hinge region (e.g., a native or modified hinge region). The Fc can be of any mammal, including human, and may be post-translationally modified (e.g., by glycosylation). In a non-limiting example, the Fc region is the region of human IgG1 and has the amino acid sequence of SEQ ID NO: 7.

The term "inflammation" will be understood by those skilled in the art to include any condition characterized by a localized protective response elicited by infection, and which is manifest by heat, swelling, pain, redness, dilation of blood vessels and/or increased blood flow, invasion of the affected area by white blood cells, loss of function and/or any other symptoms known to be associated with the inflammatory condition. For the purpose of the specification and claims, the term "inflammation" refers to an accumulation, up-regulation and/or induction of pro-inflammatory agents (e.g., cells, cytokines, and chemokines) in a tissue and/or organ (e.g., the lung) of a subject.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., fusion protein of the present disclosure), such as molar concentration, mass concentration, volume concentration, molality, mole fraction, mass fraction and mixing ratio. Specifically, the term "therapeutically effective amount" used in connection with fusion protein described herein refers to the quantity of fusion protein, which is sufficient to alleviate or ameliorate the symptoms associated with the IAV infection in the subject. Persons having ordinary skills could calculate the human equivalent dose (HED) for the medicament (such as the present fusion protein) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that is treatable with methods of the present invention. The term "subject" is intended to refer to both the male and female gender unless one gender is specifically indicated.

As IAV infection might cause severe tissue damage and lead to a threat to the human population, the object of the present disclosure aims at providing a method for protecting the human population from the illness associated with IAV infection.

Accordingly, the first aspect of the present disclosure is directed to a method useful in the treatment or prophylaxis of IAV infection in a subject. The method comprises administering to the subject a therapeutically effective amount of a fusion protein, which comprises a functional peptide and a human IgG1 Fc region. According to certain embodiments of the present disclosure, the functional peptide is a heparin sulfate proteoglycan binding domain (HBD) peptide of human DcR3 protein. To generate the fusion protein comprising HBD peptide and human IgG1 Fc region (designated as HBD.Fc), the polynucleotide of SEQ ID NO: 1 encoding HBD peptide is constructed in frame to the 5'-end of the polynucleotide of SEQ ID NO: 3 encoding human IgG1 Fc region in an expression vector. As could be appreciated by persons having ordinary skill in the art, the expression vector could be any vector suitable to express exogenous genes; for example, the vector can be pcDNA3 or pBacPAK9. In one embodiment of the present disclosure, the expression vector used to express the fusion protein HBD.Fc is pcDNA3, which is then transfected into mammalian cells to expression the fusion protein. According to the expression system commonly used in the laboratory, the mammalian cells can be FreeStyle 293-F cells. The produced fusion protein HBD.Fc thus comprises a HBD peptide and a human IgG1 Fc region respectively having the amino acid sequences of SEQ ID NOs: 4 and 7.

According to other embodiments of the present disclosure, the fusion protein comprises a human DcR3 protein and a human IgG1 Fc region (designated as DcR3.Fc). With the similar construction procedure, the polynucleotide of SEQ ID NO: 2 encoding DcR3 protein is constructed in frame to the 5'-end of the polynucleotide of SEQ ID NO: 3 encoding human IgG1 Fc region in an expression vector. As described above, the expression vector can be any vector capable of expressing exogenous genes. In one working example of the present disclosure, the expression vector used to express the fusion protein DcR3.Fc is pBacPAK9, which is then transfected into insect cells to generate the fusion protein. Examples of suitable insect cells include, but are not limited to, Sf9, Sf21, and High-Five cell. According to one preferred example, the insect cells is Sf21 cells. The produced fusion protein DcR3.Fc thus comprises a DcR3 protein and a human IgG1 Fc region coupling together; more specifically, the human IgG1 Fc region having the amino acid sequence of SEQ ID NO: 7, and the DcR3 protein is composed of a N-terminal peptide consisting of SEQ ID NO: 5, a HBD peptide consisting of SEQ ID NO: 4, and a C-terminal peptide consisting of SEQ ID NO: 6, in which the N-terminal and C-terminal peptides are respectively disposed at and connected to the upstream and downstream of the HBD peptide consisting of SEQ ID NO: 4.

As introduced above, IAV infection would cause severe tissue damage, including the pulmonary injury characterized by massive leukocyte infiltration accompanied with high levels of inflammatory cytokines. Thus, the second aspect of the present disclosure provides a method of ameliorating pulmonary injury in a subject in need thereof; specifically, the pulmonary injury is caused by excessive inflammation associated with IAV infection. The method comprises administering to the subject a therapeutically effective amount of a fusion protein. In one example, the fusion protein is HBD.Fc, which comprises a HBD peptide consisting of SEQ ID NO: 4, and a human IgG1 Fc region of SEQ ID NO: 7, coupling together. In another example, the fusion protein is DcR3.Fc, which comprises a DcR3 protein and a human IgG1 Fc region, coupling together; the human IgG1 Fc region has the amino acid sequence of SEQ ID NO: 7, and the DcR3 protein is composed of a N-terminal peptide consisting of SEQ ID NO: 5, a HBD peptide consisting of SEQ ID NO: 4, and a C-terminal peptide consisting of SEQ ID NO: 6, in which the N-terminal and C-terminal peptides are respectively disposed at and connected to the upstream and downstream of the HBD peptide consisting of SEQ ID NO: 4.

According to one embodiment of the present disclosure, the present methods are useful in treating or preventing IAV infection and/or IAV infection-associated symptoms (e.g., pulmonary injury), in which the IAV can be any of H1N1, H2N2, H3N2, H5N1, H7N7, H1N2, H9N2, H7N2, H7N3, H10N7 or H7N9. In one preferred example, the IAV is H1N1.

According to the embodiments of the present disclosure, the therapeutically effective amount of the present fusion protein is about 0.5 to 5 mg/Kg body weight per dose. For example, the amount can be 0.5, 0.6, 0.7, 0.8, 0.9, 1.0, 1.5, 2.0, 2.5, 3.0, 3.5, 4.0, 4.5, or 5.0 mg/Kg body weight of the subject. In one preferred example, the therapeutically effective amount of the present fusion protein is about 0.8 to 1 mg/Kg body weight per dose. To produce a therapeutic effect on the subject, the total dosage for a full course of treatment of the fusion protein is about 1 to 10 mg/Kg body weight; preferably, the total dosage is about 1.6 to 2 mg/Kg body weight of the subject.

To exert the method of the present disclosure, the fusion protein could be administrated by a route selected from the group consisting of oral, enteral, nasal, topical, transmucosal, and parenteral administration, in which the parental administration is any of intramuscular, intravenous, or intraperitoneal injection. In one of the preferred embodiment, the fusion protein is administrated intravenously.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Cell Culture

The FreeStyle 293-F cells purchased from Invitrogen. Inc. were cultured in FreeStyle 293 Expression Medium (Invitrogen) and incubated in a 37° C. incubator containing a humidified atmosphere of 8% $CO_2$ in air on an orbital shaker platform rotating at 135 rpm. Sf21 cells were cultured in TNM-FH medium containing 10% heat-inactivated fetal bovine serum (FBS) and incubated at 37° C., 5% $CO_2$.

Animals

Eight- to twelve-week old wild-type C57BL/6 (NLAC) and DcR3-Tg mice (bred in house on the C57BL/6 background) were used. The DcR3-Tg mice were characterized in that DcR3 was constitutively expressed and the expression was routinely confirmed by a serum ELISA. The DcR3-Tg mice were obtained in accordance with Tai et al. ("Decoy receptor 3 enhances tumor progression via induction of tumor-associated macrophages", Journal of Immunology 2012, 188, p 2464-2471). All animals were bred and housed at the Yang-Ming University Animal Center. Experimental protocols conducted in the studies were approved by the institutional animal care and welfare committee of National Yang-Ming University.

Construction

To construct the plasmid pBacPAK9-DcR3.Fc that is used to express the fusion protein DcR3.Fc, the open reading frame of the human DcR3 gene was isolated by RT-PCR using the forward primer of SEQ ID NO: 8 and the reverse primer of SEQ ID NO: 9. The amplified product was ligated in-frame into the EcoRI-cut pUC19-IgG1-Fc vector containing the cDNA of the human IgG1 Fc. The fusion gene was then subcloned into the pBacPAK9 vector (Clontech Laboratories, Palo Alto, Calif.) so as to produce the plasmid pBacPAK9-DcR3.Fc. As to construct the plasmid pcDNA3-HBD.Fc used to express the fusion protein HBD.Fc, which corresponds to the GAG binding motif of DcR3, complementary oligonucleotides of SEQ ID NOs: 10 and 11 were annealed to generate a dsDNA fragment, followed by phosphorylation of the 5-hydroxyl terminus by T4 polynucleotide kinase (New England Biolabs). The phosphorylated DNA fragment was subcloned into HincII-cut pBluescript II KS, followed by digestion with HindIII, then ligated in-frame with HindIII-cut pFlag-CMV1 (Sigma-Aldrich). The Flag-tagged DcR3_HBD was amplified by PCR and ligated in-frame with the Fc portion of hIgG1 in pcDNA3 so as to produce the plasmid pcDNA3-HBD.Fc.

Production of Fusion Protein

To produce the fusion protein DcR3.Fc, the plasmid pBacPAK9-DcR3.Fc was transfected with a linearized BacPAK6 DNA (Clontech Laboratories) into Sf21 cells to generate a recombinant virus, which comprised the genes of DcR3 and human IgG1 Fc region and was capable of replicating in Sf21 cells. The recombinant virus was then used to infect Sf21 cells, in which massive fusion proteins were produced during the viral replication process. The fusion proteins collected from the supernatant of virus-infected Sf21 cells were purified by protein-A Sepharose beads (Amersham Biosciences) followed by elution with 0.1 M glycine buffer (pH 3.0) and dialysis against PBS.

As to the production of fusion protein HBD.Fc, the plasmid pcDNA3-HBD.Fc was transfected into FreeStyle 293-F cells according to the manufacturer's instructions. Culture media collected from the transfected cells were incubated with protein A-Sepharose beads, and the bound proteins were then eluted with 0.1 M glycine buffer (pH 3.0), followed by dialysis against PBS.

Infecting the Mice with IAV

IAV (A/Puerto Rico/8/34, H1N1; PR/8) used for murine infection was grown in Madin-Darby canine kidney cells (MDCK, ATCC®CCL-34™) according to a standard procedure. Supernatant of the infected-cells was stored at −80° C. while the virus titer was determined by a plaque assay on confluent MDCK cells.

Mice were intraperitoneally injected with sodium pentobarbital before intranasal inoculation of $10^4$ PFU of IAV in 20 µl PBS. At day 4 post-infection, trachea was cannulated with a polyethylene tube and lavaged 3 times with a total volume of 3 ml PBS. Approximate 2.5 ml of instilled fluid was consistently recovered, and the supernatant was subjected to cell counting by a hemocytometer, or subjected to ELISA to determine cytokine level after centrifugation. Mice serum was obtained from the blood collected by retroorbital bleeding, while lung tissue from the sacrificed mice was fixed in 10% formalin and embedded in paraffin, followed by slicing in 5-mm-thick for immunohistochemical analysis with anti-DcR3 antibody (3H5). To determine the protective effect of fusion proteins, WT C57BL/6 mice (10-12 weeks) were inoculated with IAV ($5 \times 10^3$ PFU) intranasally in conjunction with IgG1 (20 µg/mouse), DcR3.Fc (20 µg/mouse), or HBD.Fc (20 µg/mouse) injecting via tail vein at day 0 and 3 post infection. Body weights and survivals of mice were monitored daily or at least every second day.

Determination of Cytokine Levels by ELISA

ELISA kits (R&D Systems) were used to determine the respective levels of DcR3, TNF-α, IL-1β, IL-6, IFN-α, and MCP-1 in the mouse serum and BALF according to the manufacturer's instructions. All samples were stored at −80° C. prior to an ELISA.

Flow Cytometry Analysis

Cells from BALF were stained with a panel of fluorescently conjugated antibodies (BD Biosciences). The following antibodies were used: allophycocyanin-conjugated anti-mouse F4/80, CD8, and NK1.1 antibodies; FITC-conjugated anti-mouse CD4, B220 and GR1 antibodies. Stained cells were analyzed using a FACSCalibur™ flow cytometer (BD Biosciences), and data were analyzed using CellQuest™ software (Becton Dickinson).

Statistical Analysis

Values are expressed as mean±standard error of mean (S.E.M.). All experiments were evaluated by Student t test from the Prism software package (GraphPad Version 5.00), and a 2-tailed p value of <0.05 was considered significant.

Example 1 Suppression of IAV-Induced Inflammatory Response in DcR3-Tg Mice

CD68 promoter-driven DcR3 transgenic (DcR3-Tg) mice were used to evaluate the protective effect of DcR3 protein on IAV infection and its associated symptoms, while wild-type (WT) mice served as the control, for their genomes do not contain DcR3 genes. Both groups of mice were intranasally inoculated with IAV; then the cell infiltration and cytokine levels in bronchoalveolar lavage fluid (BALF) were followed for up to 7 days. Results are depicted in FIGS. 1 to 4.

Figure 1B:
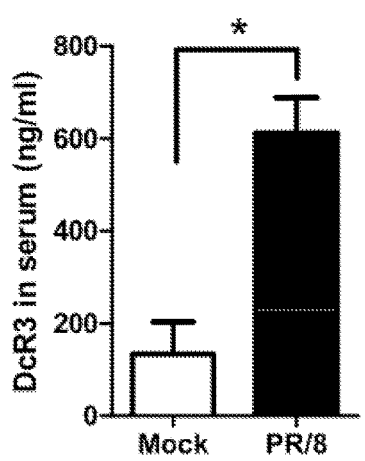
Figure 1C:
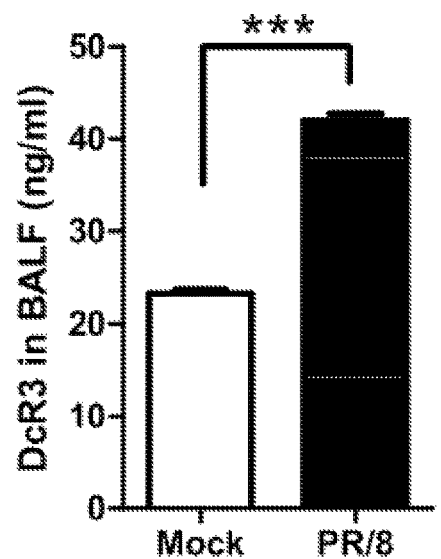
Figure 2A:
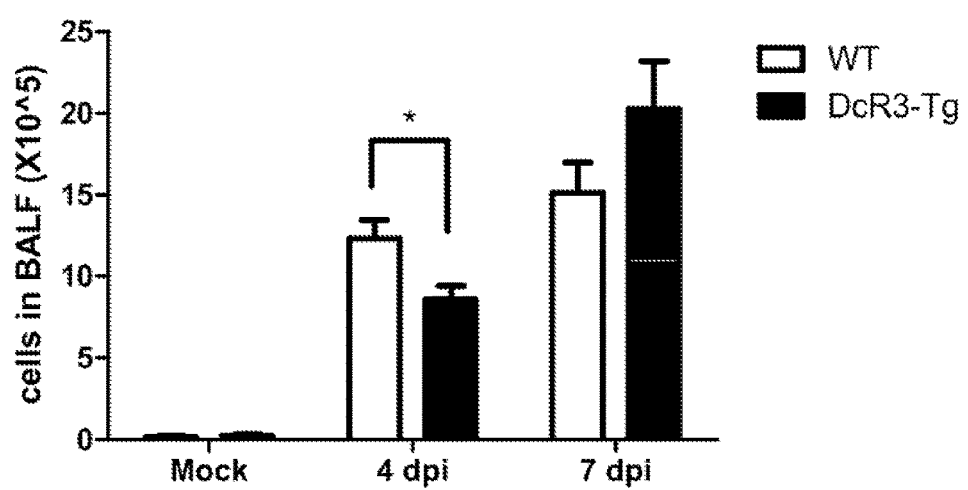
FIGS. 2A-2G are ELISA data depicting the cell number of total cell (FIG. 2A), macrophage (FIG. 2B), neutrophil (FIG. 2C), CD4$^+$ T cell (FIG. 2D), CD8$^+$ T cell (FIG. 2E), B cell (FIG. 2F), or NK cell (FIG. 2G) in BALF of WT and DcR3-Tg mice respectively infected with IAV according to Example 1 of the present disclosure.
Figure 2B:
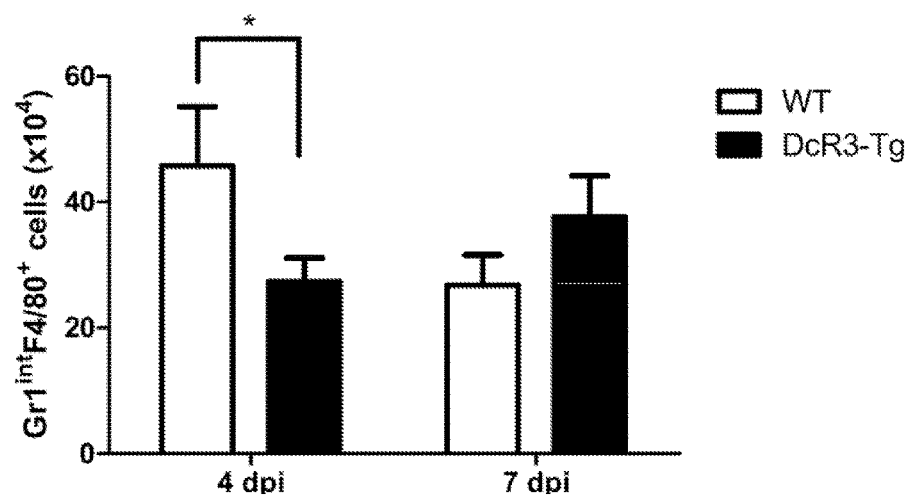
Figure 2C:
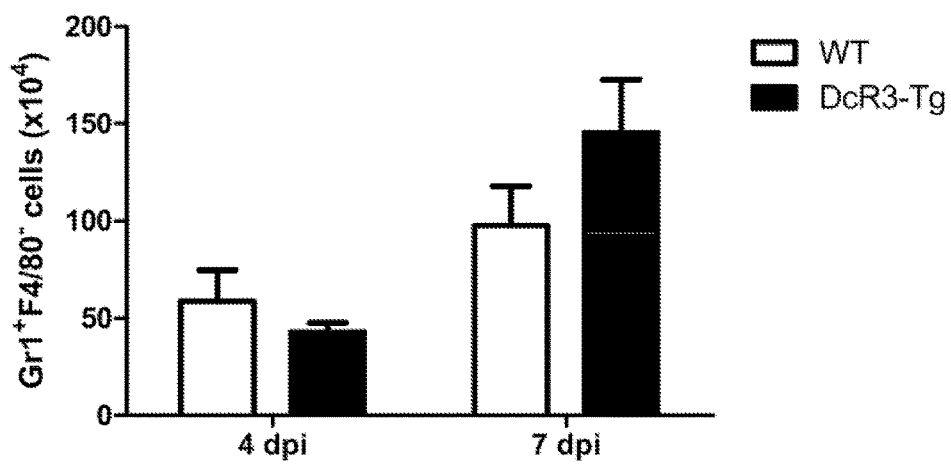
Figure 2D:
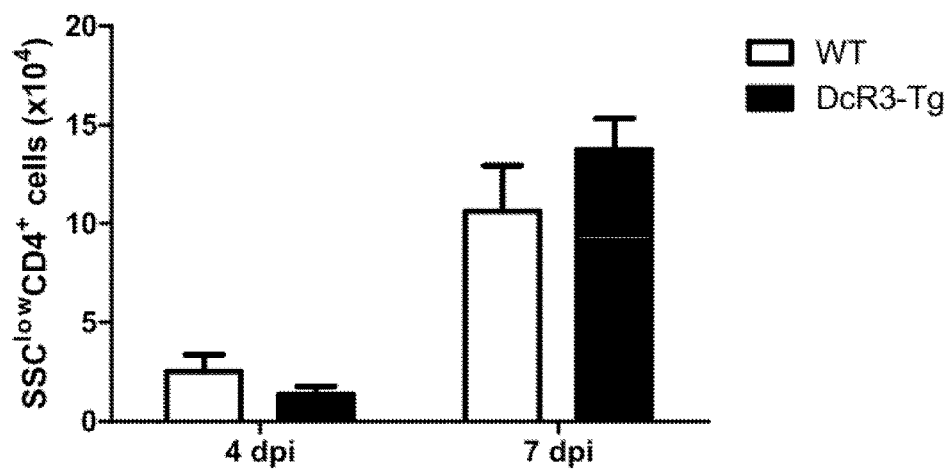
Figure 2E:
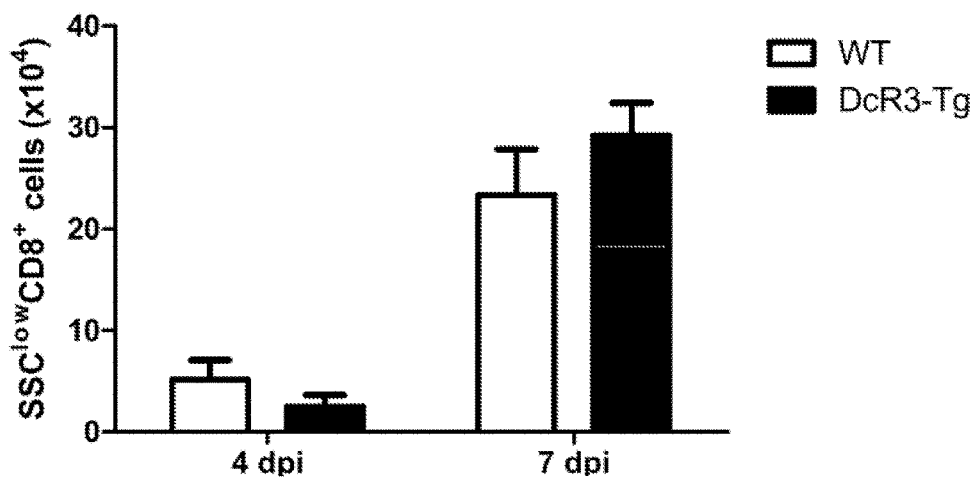
Figure 2F:
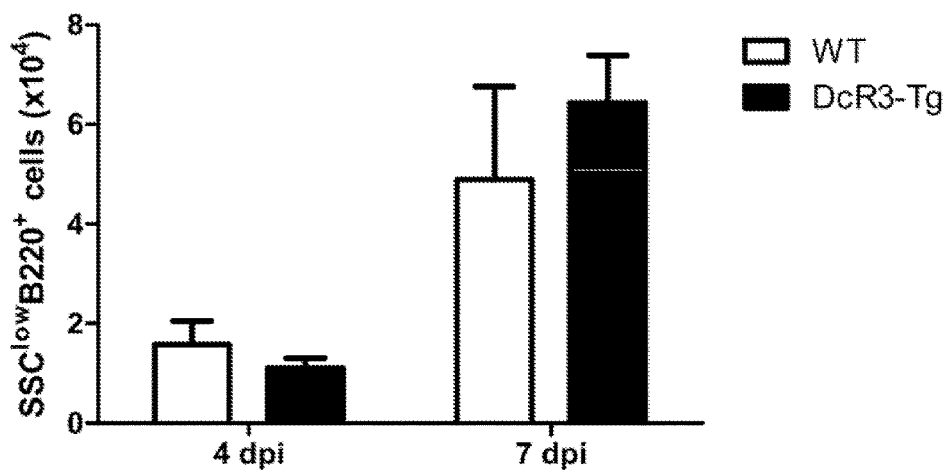
Figure 2G:
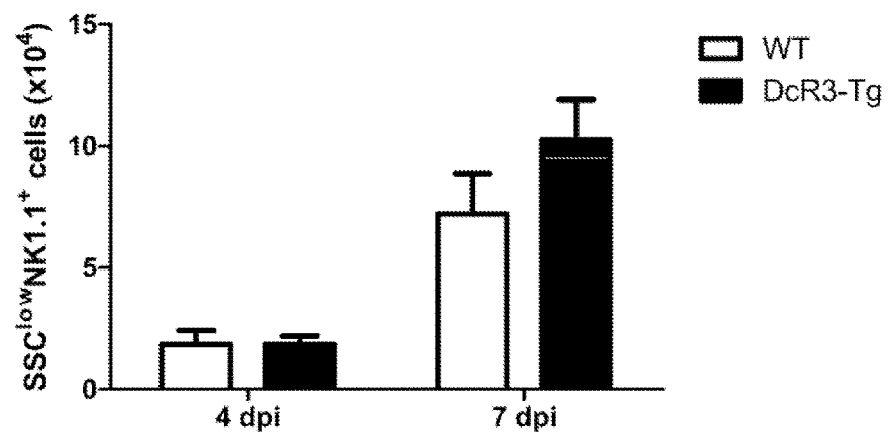
Figure 3A:
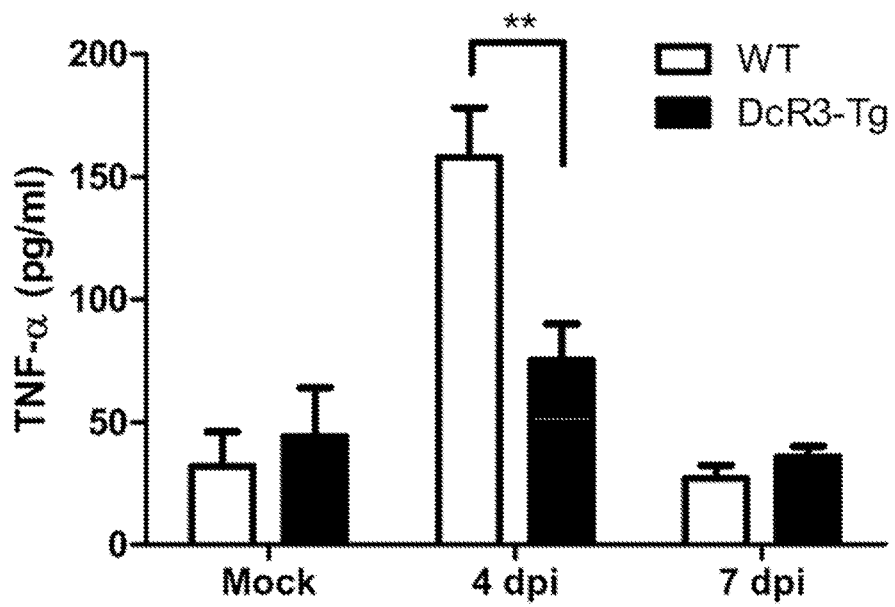
FIGS. 3A-3E are ELISA data depicting the expression of tumor necrosis factor-alpha (TNF-α, FIG. 3A), interleukin-6 (IL-6, FIG. 3B), IL-1β (FIG. 3C), interferon-alpha (IFN-α, FIG. 3D), or monocyte chemoattractant protein-1 (MCP-1, FIG. 3E) in BALF of WT and DcR3-Tg mice respectively infected with IAV according to Example 1 of the present disclosure.
Figure 3B:
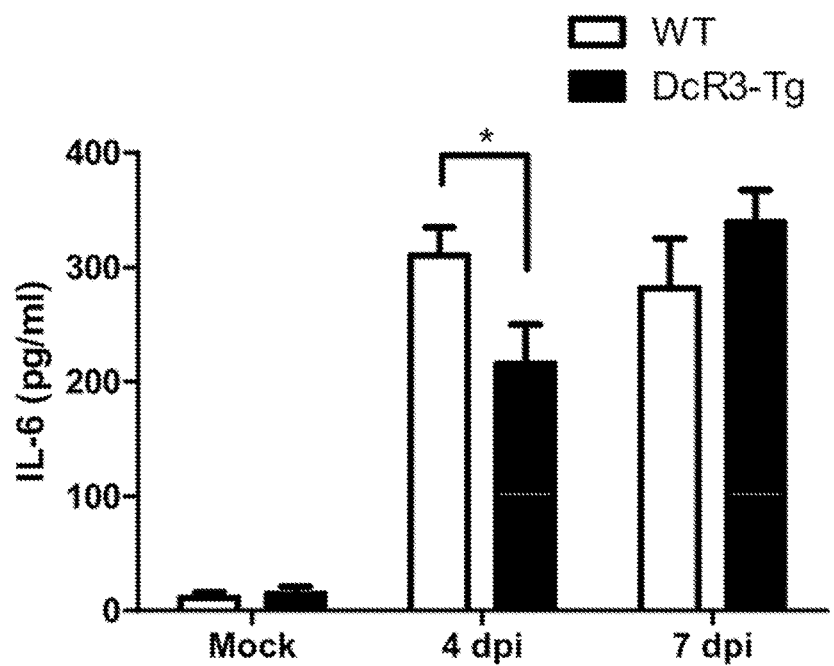
Figure 3C:
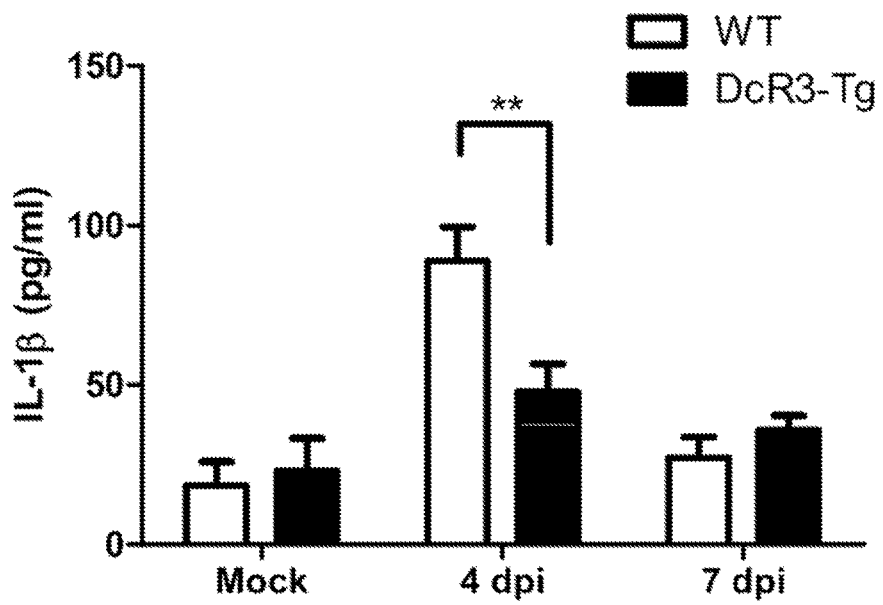
Figure 3D:
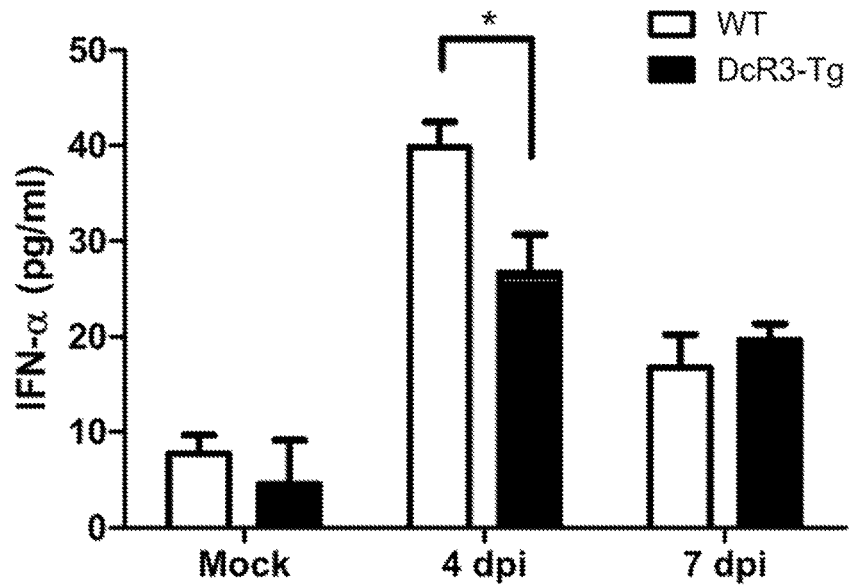
Figure 3E:
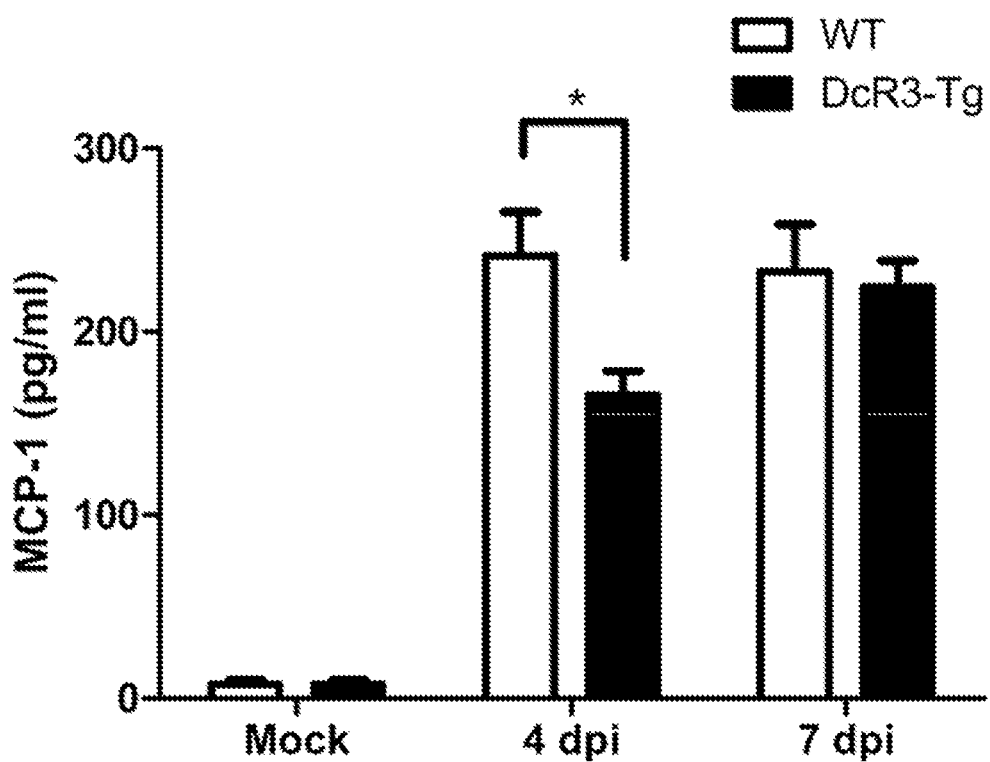
Figure 4A:
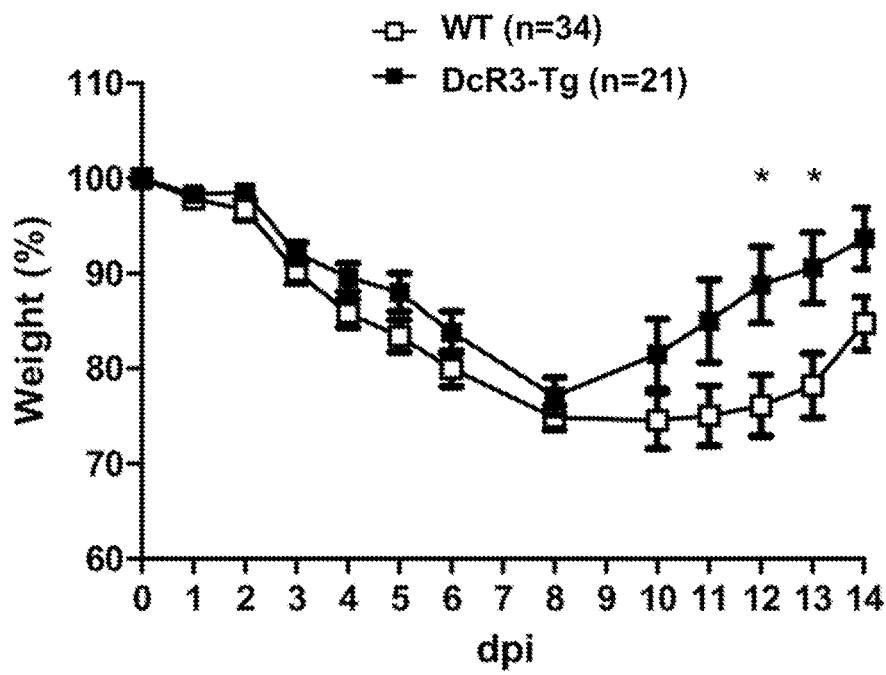
FIGS. 4A-4B are line charts respectively depicting the body weights (FIG. 4A) and the percentage of survival (FIG. 4B) of WT and DcR3-Tg mice, in which the mice were respectively infected with IAV, and the body weights were monitored for 14 consecutive days after infection according to Example 1 of the present disclosure.
Figure 4B:
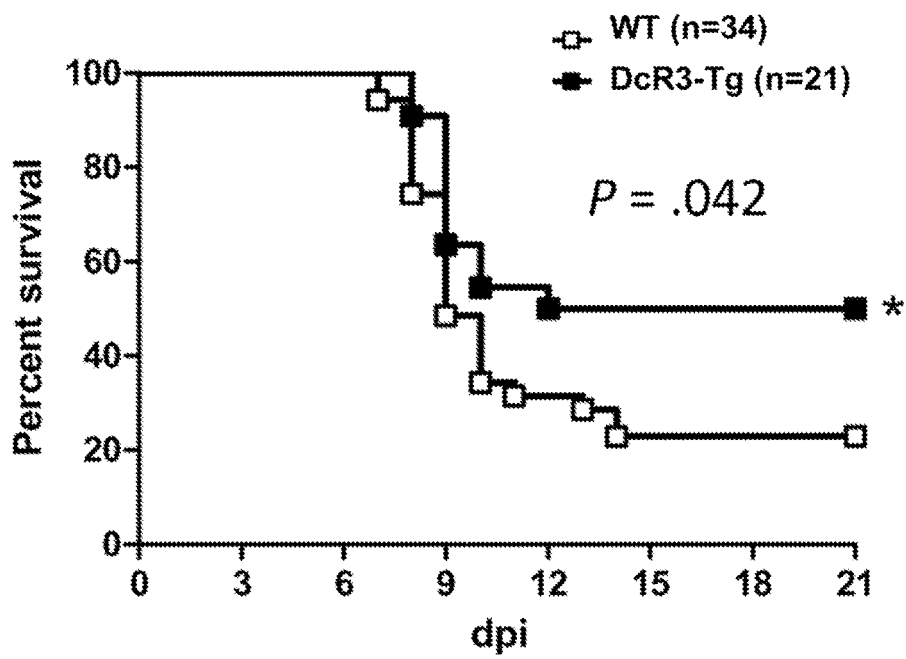

As depicted in FIG. 1A, neither mock-infected nor IAV-infected WT mice (respectively designated as WT/Mock and WT/PR/8 in FIG. 1A) expressed DcR3 protein. In contrast, DcR3 was detected in pulmonary myeloid cells, serum, and BALF of DcR3-Tg mice; and IAV infection further increased its expression (FIGS. 1A-1C). The levels of pulmonary infiltration of total cell (FIG. 2A) and $Gr1^{int}F4/80^+$ macrophage (FIG. 2B) were reduced on day 4 post infection (dpi), but returned to the same level as those of the WT on day 7 post infection; while the pulmonary infiltration of neutrophil (FIG. 2C), $CD4^+$ T cell (FIG. 2D), $CD8^+$ T cell (FIG. 2E), B cell (FIG. 2F) or NK cell (FIG. 2G) remained relatively the same as those of the control mice. In addition, the secretion of TNF-α (FIG. 3A), IL-6 (FIG. 3B), IL-1β (FIG. 3C), IFN-α (FIG. 3D), and MCP-1 (FIG. 3E) also decreased on day 4 post infection. Compared to WT littermates, body weight recovery was much faster in DcR3-Tg mice from day 8 post infection (FIG. 4A). Moreover, the survival rate of DcR3-Tg mice was also higher than that of WT littermates (50% vs. 22%, p=0.042, FIG. 4B).

The data indicated that DcR3 could effectively suppress IAV-induced inflammatory response, such as inflammatory cytokine secretion and inflammatory cell (especially macrophage) infiltration into lung tissue, at acute stage, and accordingly, provide a protection against the life-threatening illness caused by IAV.

Figure 5A:
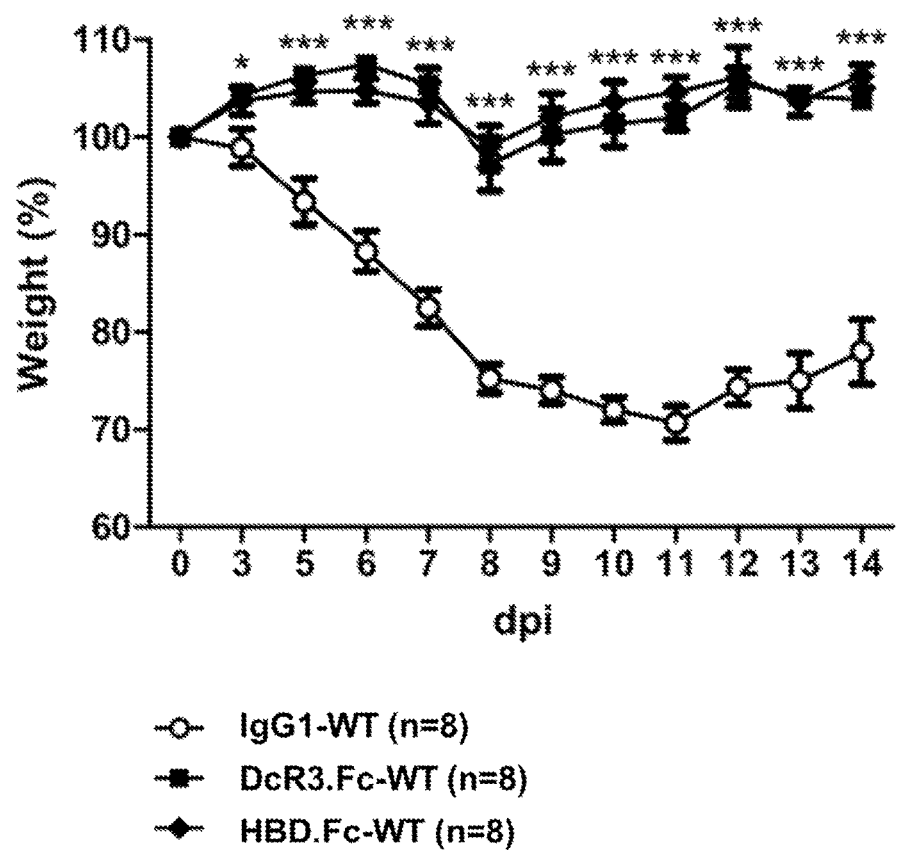
FIGS. 5A-5B are line charts respectively depicting the body weights (FIG. 5A) and the percentage of survival (FIG. 5B) of wild-type mice, in which the mice were infected with IAV and respectively treated with IgG1, DcR3.Fc, and HBD.Fc; the body weights were monitored for 14 consecutive days after infection according to Example 2 of the present disclosure.
Figure 5B:
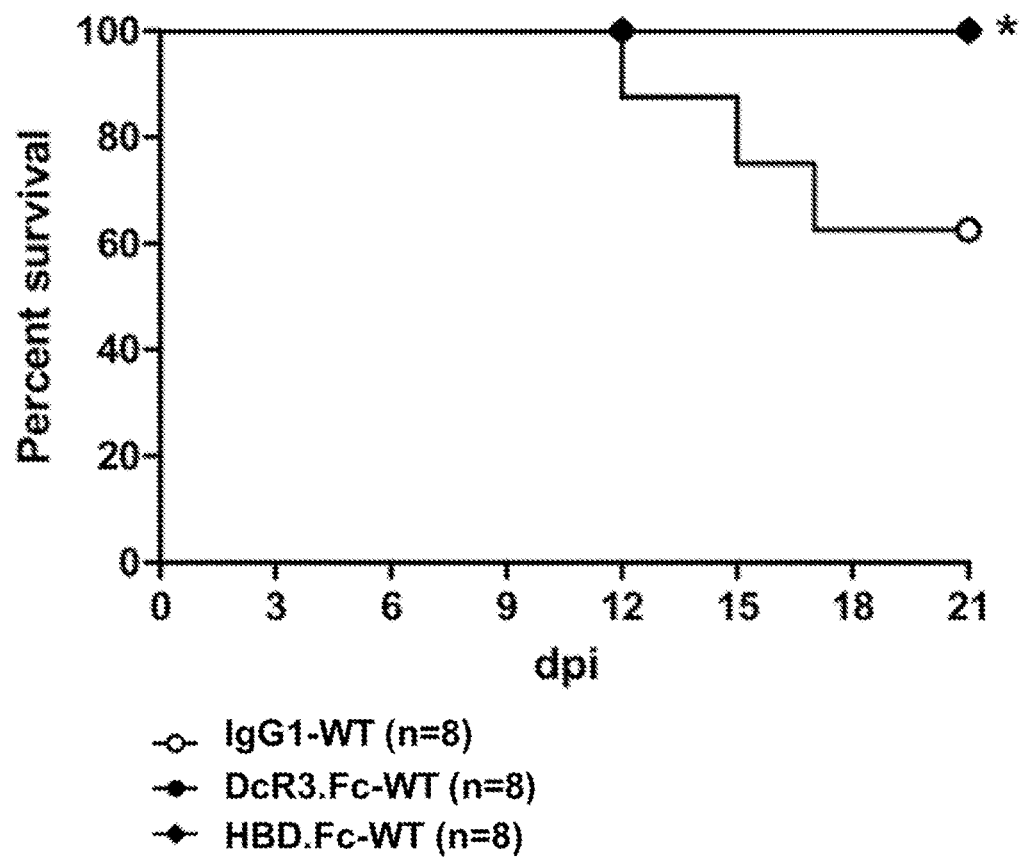

Example 2 Suppression of IAV-Induced Inflammatory Response by DcR3 Fusion Protein To further examine the protective effect of DcR3 against IAV infection, WT mice were intranasally inoculated with IAV and respectively intravenously treated with IgG1, DcR3.Fc, or HBD.Fc on day 0 and 3 post infection, in which IgG1 served as a negative control. As depicted in FIG. 5A, for mice treated with IgG1, the reduction in their body weights exhibited the similar pattern as that of the WT mice observed in FIG. 4A. In contrast, the body weights of mice treated with fusion protein DcR3.Fc or HBD.Fc remained relatively unchanged after IAV infection (FIG. 5A). Furthermore, the mice treated with DcR3.Fc or HBD.Fc exhibited a longer survival period, as compared with that of the mice treated with IgG1 (100% vs. 62.5%, p=0.0277, FIG. 5B).

The results suggested that the fusion protein DcR3.Fc or HBD.Fc could ease the symptoms related to IAV infection, and protect a subject from IAV infection.

In conclusion, the present disclosure provides a method for the treatment or prophylaxis of IAV infection via suppressing the IAV-induced inflammatory response, which would intimidate the health or even the life of a subject. Both DcR3.Fc and HBD.Fc disclosed herein are capable of suppressing the pulmonary inflammation induced by IAV and exhibit therapeutic and/or protective effect on subjects suffering from IAV infection.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of suppressing influenza A virus-induced inflammatory response in a subject comprising administering to the subject a therapeutically effective amount of a fusion protein, which comprises a first peptide consisting of SEQ ID NO: 4, and a human IgG1 Fc region coupling to the first peptide.

2. The method of claim 1, wherein the fusion protein further comprises a second peptide consisting of SEQ ID NO: 5 and a third peptide consisting of SEQ ID NO: 6, in which the second and third peptides are respectively disposed at and connected to the upstream and downstream of the first peptide consisting of SEQ ID NO: 4.

3. The method of claim 1, wherein the therapeutically effective amount is about 0.5 to 5 mg/Kg body weight per dose.

4. The method of claim 3, wherein the therapeutically effective amount is about 0.8 to 1 mg/Kg body weight per dose.

5. The method of claim 1, wherein the therapeutically effective amount is about 1 to 10 mg/Kg body weight for a full course of treatment.

6. The method of claim 5, wherein the therapeutically effective amount is about 1.6 to 2 mg/Kg body weight for a full course of treatment.

7. The method of claim 1, wherein the fusion protein is administrated by a route selected from the group consisting of oral, enteral, nasal, topical, transmucosal, and parenteral administration.

8. The method of claim 7, wherein the parental administration is any of intramuscular, intravenous, or intraperitoneal injection.

9. A method of ameliorating a pulmonary injury, wherein the pulmonary injury is caused by excessive inflammation associated with influenza A virus infection, in a subject in need thereof, comprising, administering to the subject a therapeutically effective amount of a fusion protein, which comprises a first peptide consisting of SEQ ID NO: 4, and a human IgG1 Fc region coupling to the first peptide.

10. The method of claim 9, wherein the fusion protein further comprises a second peptide consisting of SEQ ID NO: 5 and a third peptide consisting of SEQ ID NO: 6, in which the second and third peptides are respectively disposed at and connected to the upstream and downstream of the first peptide consisting of SEQ ID NO: 4.

11. The method of claim 9, wherein the therapeutically effective amount is about 0.5 to 5 mg/Kg body weight per dose.

12. The method of claim 11, wherein the therapeutically effective amount is about 0.8 to 1 mg/Kg body weight per dose.

13. The method of claim 9, wherein the therapeutically effective amount is about 1 to 10 mg/Kg body weight for a full course of treatment.

14. The method of claim 13, wherein the therapeutically effective amount is about 1.6 to 2 mg/Kg body weight for a full course of treatment.

15. The method of claim 9, wherein the fusion protein is administrated by a route selected from the group consisting of oral, enteral, nasal, topical, transmucosal, and parenteral administration.

16. The method of claim 15, wherein the parental administration is any of intramuscular, intravenous, or intraperitoneal injection.

* * * * *

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: HBD Polynucleotide

<400> SEQUENCE: 1
ctgaagctgc gtcggcggct c                                    21

<210> SEQ ID NO 2
<211> LENGTH: 900
<212> TYPE: DNA
<213> ORGANISM: Artificial Sequence
<220> FEATURE:
<223> OTHER INFORMATION: DcR3 Polynucleotide

<400> SEQUENCE: 2
atgagggcgc tggaggggcc aggcctgtcg ctgctgtgcc tggtgttggc gctgcctgcc    60
ctgctgccgg tgccggctgt acgcggagtg gcagaaacac ccacctaccc ctggcgggac   120

```
gcagagacag gggagcggct ggtgtgcgcc cagtgccccc caggcacctt tgtgcagcgg        180
ccgtgccgcc gagacagccc cacgacgtgt ggcccgtgtc caccgcgcca ctacacgcag        240
ttctggaact acctggagcg ctgccgctac tgcaacgtcc tctgcgggga gcgtgaggag        300
gaggcacggg cttgccacgc cacccacaac cgtgcctgcc gctgccgcac cggcttcttc        360
gcgcacgctg gtttctgctt ggagcacgca tcgtgtccac ctggtgccgg cgtgattgcc        420
ccgggcaccc ccagccagaa cacgcagtgc cagccgtgcc cccaggcac cttctcagcc        480 agcagctcca gctcagagca gtgccagccc caccgcaact gcacggccct gggcctggcc        540
ctcaatgtgc caggctcttc ctcccatgac accctgtgca ccagctgcac tggcttcccc        600
ctcagcacca gggtaccagg agctgaggag tgtgagcgtg ccgtcatcga ctttgtggct        660
ttccaggaca tctccatcaa gaggctgcag cggctgctgc aggccctcga ggccccggag        720
ggctggggtc cgacaccaag ggcgggccgc gcggccttgc agctgaagct gcgtcggcgg        780
ctcacggagc tcctgggggc gcaggacggg gcgctgctgg tgcggctgct gcaggcgctg        840
cgcgtggcca ggatgcccgg gctggagcgg agcgtccgtg agcgcttcct ccctgtgcac        900
```

<210> SEQ ID NO 3
<211> LENGTH: 684
<212> TYPE: DNA
<213> ORGANISM: Artificial Sequence
<220> FEATURE:
<223> OTHER INFORMATION: hIgG1.Fc Polynucleotide

<400> SEQUENCE: 3

```
gacaaaactc acacatgccc accgtgccca gcacccgaac tcctgggggg accgtcagtc         60
ttcctcttcc ccccaaaacc caaggacacc ctcatgatct cccggacccc tgaggtcaca        120
tgcgtggtgg tggacgtgag ccacgaagac cctgaggtca agttcaactg gtacgtggac        180
ggcgtggagg tgcataatgc caagacaaag ccgcgggagg agcagtacaa cagcacgtac        240
cgtgtggtca gcgtcctcac cgtcctgcac caggactggc tgaatggcaa ggagtacaag        300
tgcaaggtct ccaacaaagc cctcccagcc cccatcgaga aaaccatctc caaagccaaa        360
gggcagcccc gagaaccaca ggtgtacacc ctgcccccat cccgggatga gctgaccaag        420
aaccaggtca gcctgacctg cctggtcaaa ggcttctatc ccagcgacat cgccgtggag        480
tgggagagca atgggcagcc ggagaacaac tacaagacca cgcctcccgt gctggactcc        540
gacggctcct tcttcctcta cagcaagctc accgtggaca agagcaggtg gcagcagggg        600
aacgtcttct catgctccgt gatgcatgag gctctgcaca accactacac gcagaagagc        660
ctctccctgt ctccgggtaa atag                                              684
```

<210> SEQ ID NO 4
<211> LENGTH: 7
<212> TYPE: PRT
<213> ORGANISM: Artificial Sequence
<220> FEATURE:
<223> OTHER INFORMATION: HBD Peptide

<400> SEQUENCE: 4

Leu Lys Leu Arg Arg Arg Leu
1               5

<210> SEQ ID NO 5
<211> LENGTH: 254
<212> TYPE: PRT
<213> ORGANISM: Artificial Sequence

```
<220> FEATURE:
<223> OTHER INFORMATION: DcR3-HBD Peptide

<400> SEQUENCE: 5
```

Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu
            20                  25                  30

Thr Pro Thr Tyr Pro Trp Arg Asp Ala Glu Thr Gly Glu Arg Leu Val
        35                  40                  45

Cys Ala Gln Cys Pro Pro Gly Thr Phe Val Gln Arg Pro Cys Arg Arg
    50                  55                  60

Asp Ser Pro Thr Thr Cys Gly Pro Cys Pro Pro Arg His Tyr Thr Gln
65                  70                  75                  80

Phe Trp Asn Tyr Leu Glu Arg Cys Arg Tyr Cys Asn Val Leu Cys Gly
                85                  90                  95

Glu Arg Glu Glu Glu Ala Arg Ala Cys His Ala Thr His Asn Arg Ala
                100                 105                 110

Cys Arg Cys Arg Thr Gly Phe Phe Ala His Ala Gly Phe Cys Leu Glu
            115                 120                 125

His Ala Ser Cys Pro Pro Gly Ala Gly Val Ile Ala Pro Gly Thr Pro
    130                 135                 140

Ser Gln Asn Thr Gln Cys Gln Pro Cys Pro Pro Gly Thr Phe Ser Ala
145                 150                 155                 160

Ser Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
            180                 185                 190

Cys Thr Ser Cys Thr Gly Phe Pro Leu Ser Thr Arg Val Pro Gly Ala
    195                 200                 205

Glu Glu Cys Glu Arg Ala Val Ile Asp Phe Val Ala Phe Gln Asp Ile
    210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln
                245                 250

```
<210> SEQ ID NO 6
<211> LENGTH: 39
<212> TYPE: PRT
<213> ORGANISM: Artificial Sequence
<220> FEATURE:
<223> OTHER INFORMATION: HBD-hIgG1.Fc Peptide

<400> SEQUENCE: 6
```

Thr Glu Leu Leu Gly Ala Gln Asp Gly Ala Leu Leu Val Arg Leu Leu
1               5                   10                  15

Gln Ala Leu Arg Val Ala Arg Met Pro Gly Leu Glu Arg Ser Val Arg
            20                  25                  30

Glu Arg Phe Leu Pro Val His
        35

```
<210> SEQ ID NO 7
<211> LENGTH: 227
<212> TYPE: PRT
<213> ORGANISM: Artificial Sequence
<220> FEATURE:
<223> OTHER INFORMATION: hIgG1.Fc Peptide
```

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 26
<212> TYPE: DNA
<213> ORGANISM: Artificial Sequence
<220> FEATURE:
<223> OTHER INFORMATION: DcR3 primer-F

<400> SEQUENCE: 8
ggaattcaag gaccatgagg gcgctg                                          26

<210> SEQ ID NO 9
<211> LENGTH: 26
<212> TYPE: DNA
<213> ORGANISM: Artificial Sequence
<220> FEATURE:
<223> OTHER INFORMATION: DcR3 primer-R

<400> SEQUENCE: 9
ggaattcgtg cacagggagg aagcgc                                          26

<210> SEQ ID NO 10
<211> LENGTH: 39
<212> TYPE: DNA
<213> ORGANISM: Artificial Sequence
<220> FEATURE:
<223> OTHER INFORMATION: complementary sequence-1

-continued

<400> SEQUENCE: 10
aagcttgggc tgaagctgcg tcggcggctc gggaagctt 39

<210> SEQ ID NO 11
<211> LENGTH: 39
<212> TYPE: DNA
<213> ORGANISM: Artificial Sequence
<220> FEATURE:
<223> OTHER INFORMATION: complementary sequence-2

<400> SEQUENCE: 11
aagcttcccg agccgccgac gcagcttcag cccaagctt 39